United States Patent

Miyano et al.

Patent Number: 5,840,014
Date of Patent: Nov. 24, 1998

[54] ENDOSCOPE

[75] Inventors: Hitoshi Miyano; Chikara Yamamoto, both of Omiya, Japan

[73] Assignee: Fuji Photo Optical Co., Ltd., Omiya, Japan

[21] Appl. No.: 994,748

[22] Filed: Dec. 19, 1997

[30] Foreign Application Priority Data

Jan. 14, 1997 [JP] Japan .................................... 9-017612

[51] Int. Cl.$^6$ ....................................................... A61B 1/00
[52] U.S. Cl. ............................................ 600/125; 600/122
[58] Field of Search .................................. 600/121, 181, 600/122, 125, 123, 124

[56] References Cited

U.S. PATENT DOCUMENTS

| | | | |
|---|---|---|---|
| 4,809,678 | 3/1989 | Klein | 600/121 |
| 5,193,525 | 3/1993 | Silverstein et al. | 600/181 |
| 5,239,981 | 8/1993 | Anapliotis | 600/122 |
| 5,325,846 | 7/1994 | Szabo | 600/121 |
| 5,377,669 | 1/1995 | Schulz | 600/121 |
| 5,518,501 | 5/1996 | Oneda et al. | 600/121 |
| 5,536,236 | 7/1996 | Yabe et al. | 600/121 |
| 5,695,448 | 12/1997 | Kimura et al. | 600/121 |
| 5,707,343 | 1/1998 | O'Hara et al. | 600/121 |
| 5,733,244 | 3/1998 | Yasui et al. | 600/121 |

FOREIGN PATENT DOCUMENTS

| | | | |
|---|---|---|---|
| 6-30894 | 2/1994 | Japan | A61B 1/00 |
| 6-38922 | 2/1994 | Japan | A61B 1/00 |
| 7-294828 | 11/1995 | Japan | G02B 23/26 |

*Primary Examiner*—Paul J. Hirsch
*Attorney, Agent, or Firm*—Ronald R. Snider

[57] ABSTRACT

A transparent material having an air-layer-purging function is disposed between a cover tip portion of a protective cover covering an inserting portion of an endoscope, and a front end face of the inserting portion of the endoscope, so as to keep illumination light from reflecting between an illumination window and the cover tip portion, thus preventing flare and ghost from being generated by this reflected light. Disposed Between a front end face 1A of an inserting portion 1 of the endoscope and a transparent cover 11 constituting a protective cover 10 for the endoscope is a transparent material 15 whose form can conform to the transparent cover 11, illumination window 2, and viewing window 3 without intervening an air layer therebetween, such as deaerated water, cedar oil, jelly-like material, gel-like material, or the like. Consequently, light reflection at the rear end face 11A of the transparent cover 11 and the front end face 2A of the transparent window 2 can be reduced, whereby the loss in quantity of the irradiation light can be decreased. Also, the quantity of the reflected light incident on the viewing window 3 can be lowered, whereby the occurrence of flare and ghost caused thereby can be alleviated.

4 Claims, 3 Drawing Sheets

ENDOSCOPE

RELATED APPLICATIONS

This application claims the priority of Japanese Patent Application No. 9-17612 filed on Jan. 14, 1997, which is incorporated herein by reference.

BACKGROUND OF THE INVENTION

1. Field of the Invention

The present invention relates to an endoscope used for medical purposes and the like, and specifically to an endoscope detachably attached with a protective cover for preventing the inserting portion of the endoscope from being contaminated.

2. Description of the Prior Art

Employed in an endoscope used for medical purposes and the like is a protective cover for keeping its inserting portion from directly coming into contact with an object to be observed, in order to prevent the inserting portion from being contaminated with dirty substances. Such a protective cover is detachably attached to the inserting portion of the endoscope so as to cover it as a whole. At the time of observation, the protective cover is used in a covered state so as to keep the inserting portion of the endoscope from directly coming into contact with the object to be observed, thus preventing the endoscope from being contaminated. Further, as the protective cover is made disposable, its user is free from the trouble of washing the inserting portion each time the endoscope is used.

At the front end face of the endoscope covered with such a protective cover, an illumination window and a viewing window, which are made of glass, plastic, or the like, are disposed adjacent to each other. Disposed inside the illumination window is an irradiation optical system for irradiating the object with illumination light guided by a light guide. Disposed inside the viewing window adjoining the illumination window are an image-forming optical system for forming an image of image information carried by a luminous flux incident through the viewing window, and an image-capturing optical system for photoelectrically converting thus formed observation image. The protective cover, whose tip portion is constituted by a transparent cover made of glass, plastic, or the like, covers the inserting portion of the endoscope of the glass so as to seal the whole outer periphery thereof and so that the front end face of the inserting portion and the transparent cover are closely in contact with each other.

Nevertheless, since the illumination and viewing windows and the transparent cover are made of rigid materials such as glass, plastic, and the like, it is difficult for them to be completely in close contact with each other, whereby air would inevitably intervene between the illumination and viewing windows and the transparent cover. When air intervenes between the illumination and viewing windows and the transparent cover, due to differences in refractive index between the material constituting the illumination window, viewing window, and transparent cover and the air, light attains a higher reflectivity in front of and behind the air layer, thus yielding a loss in the quantity of illumination light irradiating the object, whereby the object may not be irradiated with a sufficient quantity of light. Also, the light reflected in front of or behind the air layer may be made incident on the viewing window, thereby yielding flare, ghost, or the like, which keeps the object from being favorably observed.

SUMMARY OF THE INVENTION

In view of these circumstances, it is an object of the present invention to provide an endoscope which can lower loss in illumination light quantity and suppress the occurrence of flare and ghost, thus allowing the object to be favorably observed.

The present invention provides an endoscope comprising an inserting portion whose front end face is provided with an illumination window and a viewing window; and a protective cover, used as detachably covering the inserting portion, having a cover tip portion disposed in proximity to the front end face;

wherein a transparent material having an air-layer-purging function is disposed, at least, between the cover tip portion and the illumination and viewing windows.

Here, the transparent material having an air-layer-purging function refers to, for example, a liquid such as water, and a transparent material whose form can conform to the cover tip portion and the illumination and viewing windows so as to prevent an air layer (or bubble) from intervening therebetween, such jelly-like material, gel-like material, transparent grease, cedar oil, or the like having an elasticity by which the illumination window and the viewing window can come into close contact with each other.

Preferably, the transparent material is made of a liquid material.

Preferably, the whole gap region between the inserting portion and the protective cover is filled with the transparent material.

Preferably, the protective cover is configured like a bag whose one end is closed, while an open end portion of the protective cover is formed with a thick annular part having a circular cross section, which is adapted to engage with an annular groove formed in a side part of the inserting portion.

DESCRIPTION OF THE PREFERRED EMBODIMENTS

In the following, embodiments of the present invention will be explained with reference to the accompanying drawings.

Figure 1:
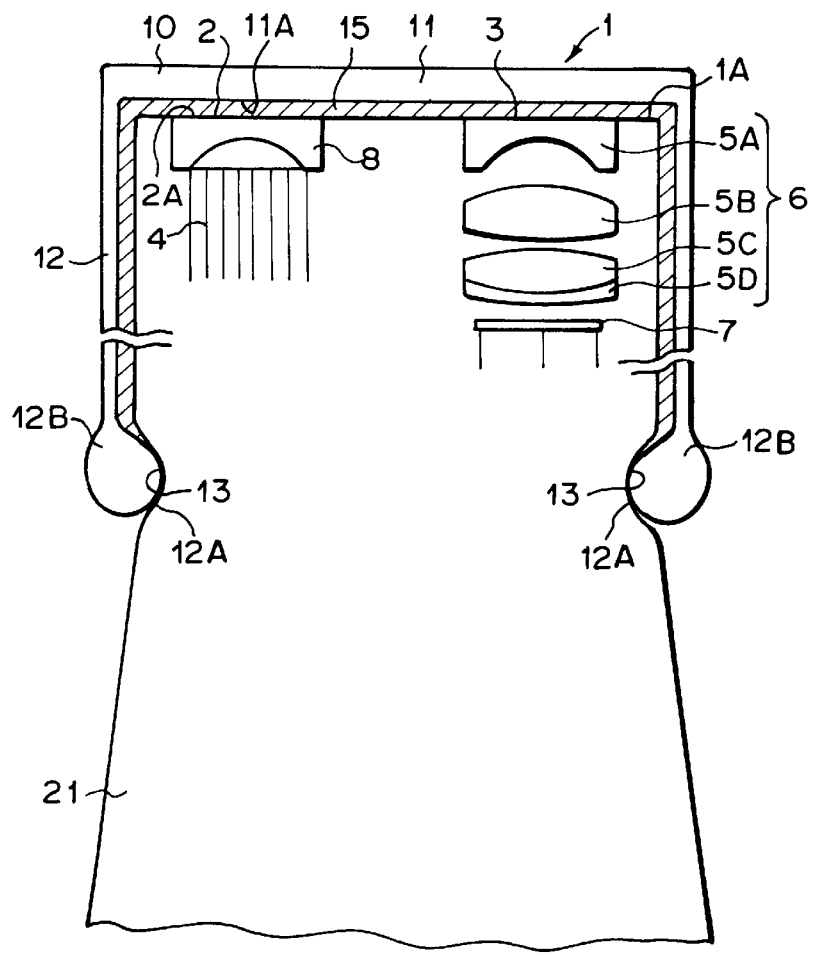
FIG. 1 is a longitudinal sectional view showing a configuration of an endoscope in accordance with an embodiment of the present invention.
Figure 2:
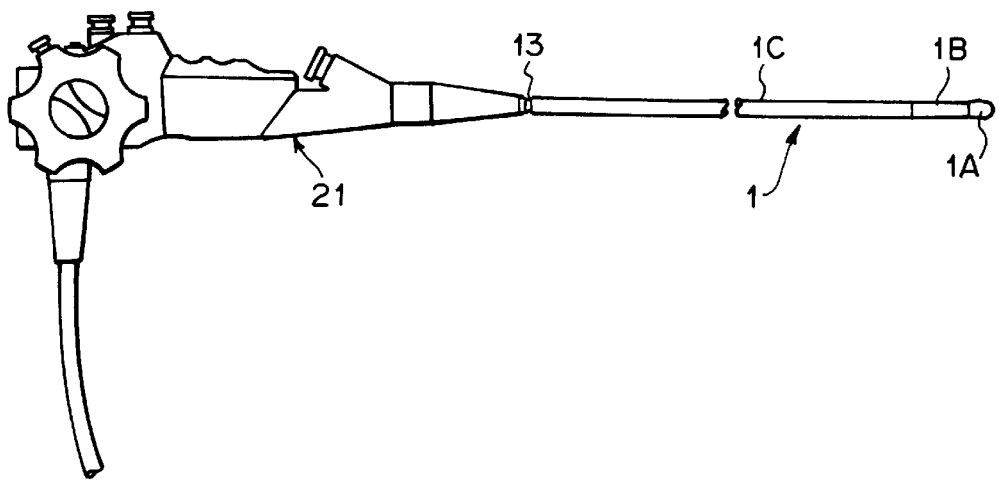
FIG. 2 is a schematic view showing an overall configuration of the endoscope in accordance with the embodiment of the present invention.
Figure 3:
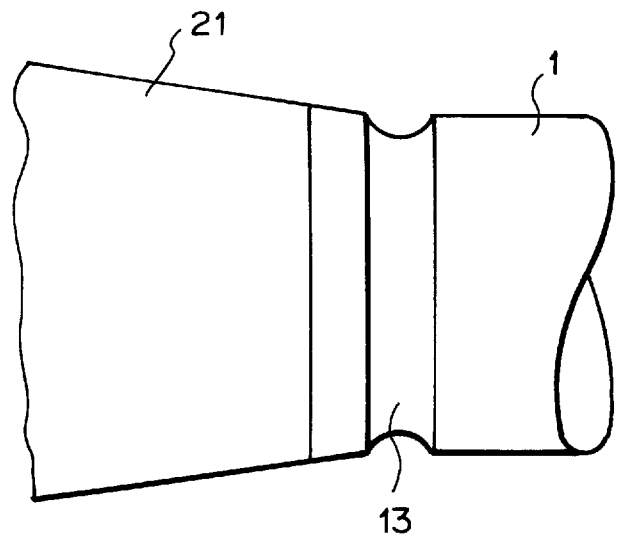
FIG. 3 is a partially enlarged view showing a main body of the endoscope shown in FIG. 2.
Figure 4:
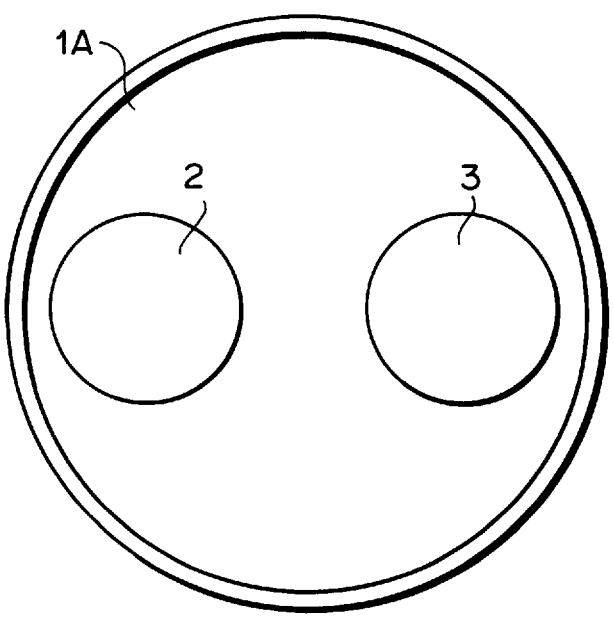
FIG. 4 is a sectional view showing a configuration of a tip portion of the endoscope in accordance with the embodiment of the present invention.

FIG. 1 is a view showing an inserting portion of an embodiment of the endoscope in accordance with the present invention. FIG. 2 is a schematic view showing the embodiment of the endoscope in accordance with the present invention as a whole. FIG. 3 is a partially enlarged view showing the embodiment of the endoscope in accordance with the present invention. FIG. 4 is a transverse sectional view showing a tip portion of the embodiment of the endoscope in accordance with the present invention.

First, with reference to FIG. 2, the overall configuration of the endoscope in accordance with the present invention will be explained. The main body of this endoscope comprises a local operating portion 21 by which an operator performs various operations, and an inserting portion 1 which is inserted into a body of a subject. The inserting portion 1 is constituted by a tip part 1A, an angle part 1B which freely bends the tip part 1A toward a site to be observed, and a long soft part 1C to be inserted into a body cavity such as gullet in particular. The whole outer peripheral part of the inserting portion 1 is covered with a protective cover 10 which will be explained later.

Also, as shown in FIG. 3, the boundary part between the local operating portion 21 of the endoscope main body and the inserting portion 1 is provided with an annular groove 13 surrounding the outer wall surface thereof, into which an open end portion of the protective cover 10 is fitted.

In the following, the configuration of the inserting portion 1 will be explained.

As shown in FIGS. 1 and 4, the tip part 1A of the inserting portion 1 is provided with an illumination window 2 and a viewing window 3 disposed adjacent to the illumination window 2. Each of the illumination window 2 and viewing window 3 is made of glass, plastic, or the like. Disposed inside the illumination window 2 is an irradiation optical system (not depicted) emitting illumination light which is guided to the illumination window 2 via a light guide 4 and a lens 8. Disposed inside the viewing window 3 are an image-forming optical system 6 comprising four lenses 5A to 5D for forming an observation image with respect to the viewing window 3, and an image-capturing optical system 7, such as CCD, for photoelectrically converting thus formed observation image.

The above-mentioned protective cover 10 is constituted by a transparent cover 11 closely in contact with the tip part 1A of the inserting portion 1 and a protective tube 12 covering the whole outer periphery of the inserting portion 1. The transparent cover 11 is made of a material such as glass, plastic, or the like, and is attached substantially in close contact with the tip portion 1A. The protective tube 12 is made of a flexible film-like member or thin member so as to be easily attached to and removed from the inserting portion 1. Also, an insertion opening (open end portion) 12A of the protective tube 12 is formed with an annular thick part 12B having a circular cross section, which engages with the above-mentioned annular groove 13. When the inserting portion 1 is covered with the protective tube 12, the thick part 12B fits into the groove 13 formed in the inserting portion 1, thereby preventing the protective cover 10 from dropping off.

Preferably, the protective cover 10 and inserting portion 1, the transparent cover 11 and the illumination window 2 and viewing window 3 in particular, are closely in contact with each other without any gap therebetween. Nevertheless, since the transparent cover 11, illumination window 2, and viewing window 3 are constituted by a material such as glass, plastic, or the like, it is difficult for them to completely come into close contact with each other, whereby an air layer inevitably intervenes between the transparent cover 11 and the illumination window 2 and viewing window 3. When air thus intervenes between the transparent cover 11 and the illumination window 2 and viewing window 3, due to a difference in refractive index between the air and the material such as glass, plastic, or the like constituting the illumination window 2, viewing window 3, and transparent cover 11, light attains a higher reflectivity at the front and rear interfaces of the air layer, thus yielding loss in quantity of the illumination light irradiating the object to be observed, whereby the object to be observed may not be irradiated with a sufficient quantity of light. Also, the light reflected at the front and rear interfaces of the air layer may become incident on the viewing window 3, thereby forming flare, ghost, or the like, which prevents the object from being favorably observed.

Therefore, in this embodiment, disposed in the gap formed between the protective cover 10 and the inserting portion 1 is a transparent liquid material 15, such as water, having a refractive index higher than that of air. Preferably, in order to prevent bubbling, the liquid material 15 is deaerated water. Here, the refractive index of air is 1, whereas the refractive index of water is higher than that of air so as to approach the range of 1.4 to 1.5 within which the refractive index of glass or plastic exists. Accordingly, the illumination light emanating from the illumination window 2 is less likely to be reflected by the front end face 2A of the illumination window 2 and the rear end face 11A of the transparent cover 11, and its loss in light quantity is alleviated, whereby the object to be observed can be irradiated with a sufficient quantity of light. Also, since the quantity of the light reflected by the rear end face 11A of the transparent cover 11 and the front end face 2A of the illumination window 2 becomes smaller, the reflected light incident on the viewing window 3 is reduced, whereby the occurrence of flare and ghost caused by thus reflected light can be alleviated. Accordingly, the object can be favorably observed.

In order to dispose the liquid material between the protective cover 10 and the inserting portion 1, at the time when the protective cover 10 is attached to the inserting portion 1, the inside of the protective cover 10 is filled with the liquid material 15, and then the inserting portion 1 is inserted into the cover 10. Consequently, the liquid material 15 can be disposed between the protective cover 10 and the inserting portion 1. Here, after the protective cover 10 is attached, since the thick part 12B fits into the groove 13 as mentioned above, the liquid material 15 is prevented from leaking from the protective cover 10 as well.

Figure 5:
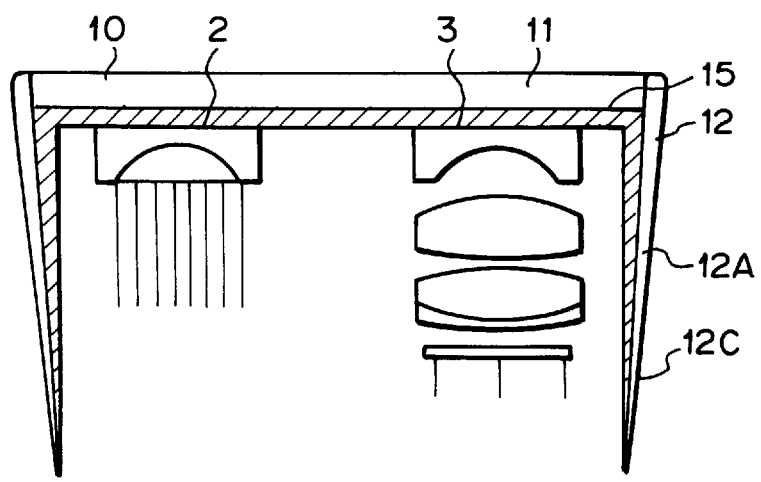
FIG. 5 is a transverse sectional view showing a configuration of the endoscope in accordance with another embodiment of the present invention.

Though the thick part 12B formed at the insertion opening 12A of the protective tube 12 constituting the protective cover 10 engages with the groove 13 formed at the inserting portion 1 in the foregoing embodiment so as to prevent the liquid material 15 from leaking and the protective cover 10 from dropping off, a tapered part 12C may be formed at the insertion opening 12A of the protective tube 12 as shown in FIG. 5. The tapered part 12C is formed such that the whole diameter of the cover 10 slightly tapers down toward the open end. Owing to this configuration, the protective tube 12 is secured to the inserting portion 1 by a certain degree of fastening force, thus making it possible to prevent the liquid material 15 from leaking and the protective cover 10 from dropping off.

Though the transparent liquid material such as water is interposed between the protective cover 10 and the inserting portion 1 in the above-mentioned embodiment; any material may be used as long as it is a transparent material whose form can conform to the transparent cover 11 and the illumination window 2 and viewing window 3 so as to prevent the air layer from intervening therebetween, such as jelly-like material, gel-like material, transparent grease, cedar oil, or the like having an elasticity by which the transparent cover 11 and the illumination window 2 and viewing window 3 can come into close contact with each other. Here, preferably used is a material whose refractive index difference with respect to the material constituting each of the transparent cover 11, illumination window 2, and viewing window 3 is small, and which has no internal strain.

Though the transparent liquid material 15 is disposed between the whole surface of the tip part 1A of the inserting portion 1 and the whole surface of the transparent cover 11 in the above-mentioned embodiment; when a material without fluidity such as the above-mentioned jelly-like material, gel-like material, or grease is used, it may be disposed at a part corresponding to the illumination window 2 and viewing window 3 without spreading over the whole surface of the tip part 1A of the inserting portion 1 and the whole surface of the transparent cover 11.

Though the above-mentioned embodiment relates to a protective cover for covering the inserting portion that is provided with only one illumination window 2, the endoscope in accordance with the present invention is also applicable to the case where two illumination windows are provided in order to increase the quantity of irradiating light.

As explained in detail in the foregoing, in the endoscope in accordance with the present invention, since a transparent material having an air-layer-purging function is disposed, at least, between the tip part of the protective cover and the illumination and viewing windows, there is no space therebetween for allowing air to intervene. Consequently, of the illumination light emanating from the illumination window, the ratio reflected by the tip part and both surfaces of the illumination window is reduced, thereby lowering the light quantity loss. Consequently, the object to be observed can be irradiated with a sufficient amount of light. Also, the light reflected by the illumination window and the tip part of the cover can be reduced, whereby the occurrence of flare and ghost caused by this reflected light can be lowered. Accordingly, the object can be observed favorably.

What is claimed is:

1. An endoscope inserting portion comprising:

a front end face having an illumination window and a viewing window;

a detachable protective covering for covering the inserting portion;

wherein said detachable protective covering is disposed in proximity to the front end face;

a space between the front end face and the detachable covering; and a transparent material for purging air from the space between the front end face and the detachable covering.

2. An endoscope according to claim 1 wherein said transparent material is made of a liquid material.

3. An endoscope according to claim 1, wherein said transparent material fills all of the space between the front end face and the detachable covering.

4. An endoscope according to claim 1, wherein said detachable protective covering is a bag with one end closed, and an open end portion which is formed with a thick annular part having a circular cross section, wherein said thick annular part engages an annular groove formed on said inserting portion.

* * * * *